(12) United States Patent
Nardini (10) Patent No.: US 9,844,403 B2
(45) Date of Patent: Dec. 19, 2017

(54) STABILIZING BONE FIXATION ELEMENT (75) Inventor: Reto Nardini, Grenchen (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1261 days.

(21) Appl. No.: 12/857,034

(22) Filed: Aug. 16, 2010

(65) Prior Publication Data
US 2011/0054476 A1 Mar. 3, 2011

Related U.S. Application Data (60) Provisional application No. 61/237,005, filed on Aug. 26, 2009.

(51) Int. Cl.
A61B 17/84 (2006.01)
A61B 17/80 (2006.01)
A61B 17/86 (2006.01)
A61B 17/00 (2006.01)

(52) U.S. Cl.
CPC ........ *A61B 17/844* (2013.01); *A61B 17/8033* (2013.01); *A61B 17/863* (2013.01); *A61B 17/8052* (2013.01); *A61B 17/8057* (2013.01); *A61B 17/866* (2013.01); *A61B 17/8635* (2013.01); *A61B 17/8665* (2013.01); *A61B 17/8685* (2013.01); *A61B 2017/00004* (2013.01); *A61B 2017/8655* (2013.01)

(58) Field of Classification Search
CPC .............. A61B 17/844; A61B 17/8685; A61B 2017/8655
USPC ........ 606/280–283, 286, 289, 290, 292–294, 606/297, 300–302, 307–310, 313, 314, 606/319, 320, 322, 326–329; 411/340, 411/345, 546, 547, 551
See application file for complete search history.

(56) References Cited

U.S. PATENT DOCUMENTS

| 2,918,841 | A | * | 12/1959 | Poupitch | 411/36 |
| 4,100,833 | A | * | 7/1978 | Nessa | 411/340 |
| 4,108,043 | A | | 8/1978 | Varga | |
| 5,244,324 | A | * | 9/1993 | Smith | 411/344 |
| 5,501,695 | A | * | 3/1996 | Anspach et al. | 606/232 |
| 6,328,758 | B1 | | 12/2001 | Tornier et al. | |
| 6,746,191 | B2 | * | 6/2004 | Edland | 411/34 |

(Continued)

FOREIGN PATENT DOCUMENTS

| GB | 2 173 565 | 10/1986 |
| WO | 92/14423 | 9/1992 |
| WO | 96/14798 | 5/1996 |

*Primary Examiner* — Matthew Lawson
*Assistant Examiner* — Amy Sipp
(74) *Attorney, Agent, or Firm* — Fay Kaplun & Marcin, LLP (57) ABSTRACT A bone fixation device includes (a) a threaded shaft extending from a proximal end to a distal end; (b) a head located at the proximal end of the shaft; (c) a connector threadably engaging the threaded shaft and movable therealong; and (d) an extension member movable between an insertion configuration for insertion through an opening in a cortex of a bone to a locked configuration when pressed against an inner surface of the cortex. The profile of the wing in the locked configuration in the plane perpendicular to the longitudinal axis of the shaft is increased relative to the insertion configuration to distribute forces transmitted between the bone fixation apparatus and the bone over an increased area of the cortex.

9 Claims, 9 Drawing Sheets (56) References Cited

U.S. PATENT DOCUMENTS

| | | | |
|---|---|---|---|
| 8,132,435 B2* | 3/2012 | Thomas et al. | 70/95 |
| 2005/0065526 A1* | 3/2005 | Drew et al. | 606/72 |
| 2008/0004711 A1 | 1/2008 | Li et al. | |
| 2008/0195096 A1* | 8/2008 | Frei | 606/60 |
| 2008/0288003 A1* | 11/2008 | McKinley | 606/313 |
| 2012/0109222 A1* | 5/2012 | Goel et al. | 606/310 |

* cited by examiner

STABILIZING BONE FIXATION ELEMENT

PRIORITY CLAIM

The present application claims priority to U.S. Provisional Application Ser. No. 61/237,005 entitled "Stabilizing Bone Fixation Element" filed on Aug. 26, 2009 to Reto Nardini, the entire disclosure of which is incorporated herein by reference.

FIELD OF THE INVENTION

The present invention is related to the field of bone fixation and, in particular, relates to a system and method for the fixation of bones via a compressible bone fixation device.

BACKGROUND

Procedures for the fixation and stabilization of bones commonly employ screws inserted through bone fixation plates situated against the outer peripheries of the bones. Such bone screws are subjected to varying loads during and after implantation. In certain cases, such bone screws may be unable to withstand the loads, resulting in screw pull-out which reduces the rigidity of the bone and leaves the bone susceptible to further fracture or injury. Furthermore, presently available bone screws are not formed to withstand the increased loads that may be applied thereto when implanted in already weakened bone, such as a fractured, porotic or otherwise damaged bone.

SUMMARY OF THE INVENTION

The present invention relates to a bone fixation device comprising a threaded shaft extending from a proximal end to a distal end and a head at the proximal end of the shaft in combination with a connector threadably engaging the threaded shaft and movable therealong and an extension member movable between an insertion configuration for insertion through an opening in a cortex of a bone to a locked configuration when pressed against an inner surface of the cortex, the profile of the wing in the locked configuration in the plane perpendicular to the longitudinal axis of the shaft being increased relative to the insertion configuration to distribute forces transmitted between the bone fixation apparatus and the bone over an increased area of the cortex.

DETAILED DESCRIPTION

The present invention is directed to a system and method for the fixation of bone in a living body. Specifically, a bone fixation device according to the present invention comprises a head and an elongated shaft with a wing element extending laterally outward from the shaft. The wing is formed as an abutment extending radially outward from the shaft and positioned along a plane extending substantially parallel to a longitudinal axis of the shaft. When a load is exerted on the bone fixation device that would otherwise cause pullout, the wing is longitudinally compressed to absorb at least a portion of this load. Furthermore, an increased width of the wing relative to the bone fixation device extends an area over which the load is distributed. The wing of the bone fixation device is configured to be inserted through an appropriately sized hole in a bone plate and rests against an inner bone cortex in an operative configuration to increase a holding force of the bone fixation device against the bone. Thus, the wing aids in maintenance of a position of the bone fixation device within a bone while maximizing a contacting surface area between the bone fixation device and an inner wall of a bone, as will be described in greater detail hereinafter. It is noted that although the present invention is described with respect to particular bones, the device may be employed in any bone without deviating from the spirit and scope of the present invention. As used in this application, the term proximal refers to a direction approaching a physician or other user of the device while the term distal refers to a direction along the device away from the user. In an operative configuration, the distal end of the device is received within the body while the proximal end remains closer to a point of insertion into the body.

Figure 1:
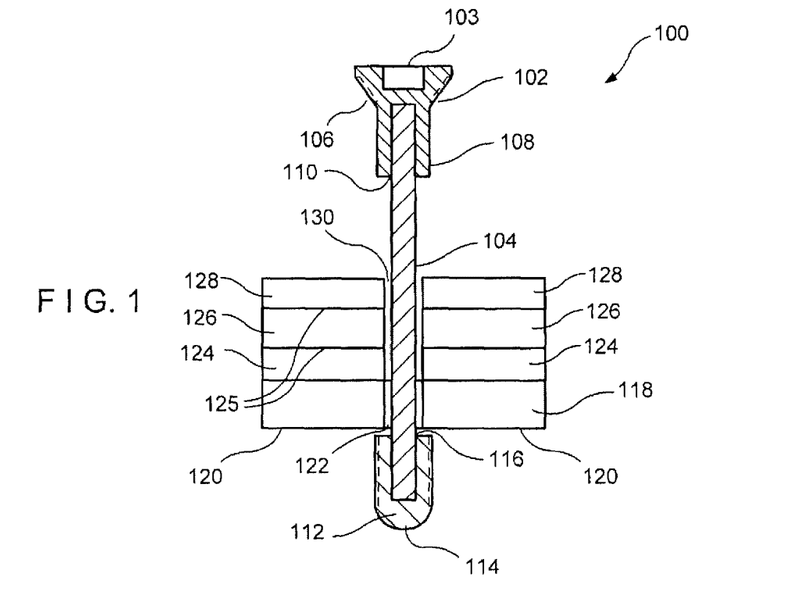
FIG. 1 shows a first partial cross-sectional view of a bone fixation device according to a first embodiment of the present invention.

FIG. 1 shows an exemplary bone fixation device 100 according to a first embodiment of the invention. The bone fixation device 100 comprises a head 102 and an elongated shaft 104 extending distally therefrom. The head 102 is formed with a taper 106 extending to a substantially cylindrical extension 108 extending distally therefrom. An opening 110 formed at a distal end of the extension 108 permanently receives a proximal portion of the shaft 104. A proximal face of the head 102 further comprises a recess 103 configured to receive a respectively shaped tip of a driver (not shown) used to drive the bone fixation device 100 into the bone. The extension 108 of the head 102 is formed with a greater diameter than a diameter of the shaft 104 and further comprises threading (not shown) along an outer periphery thereof to permit screwing of the bone fixation device 100 into a plate hole, as will be described in greater detail below. In one embodiment of the present invention, the head 102 may be threaded to engage a respectively shaped threading of a plate hole in which the bone fixation device 100 is to be inserted. The shaft 104 is formed with a predetermined length selected to conform to the requirements of a procedure being performed on a target bone as those skilled in the art will understand. The shaft 104 includes a tip 112 extending distally therefrom to a distal end 114 of the device 100. In one embodiment of the invention, the tip 112 may comprise a smooth outer surface which may be slidably inserted past a bone plate hole, as will be described in greater detail later on. In another embodiment, the tip 112 may be provided with threading to increase an axial holding strength thereof within the bone. Specifically, the threaded tip 112 may be screwably inserted past the bone plate hole and into a target portion of bone, the threaded engagement with the bone increasing a mechanical pull out resistance of the bone fixation device 100, as those skilled in the art will understand. The tip 112 may also comprise an opening 116 configured to permit permanent insertion of a distal portion of the shaft 104 therein. The bone fixation device 100, including the head 102, shaft 104 and tip 112 may be formed of stainless steel, titanium, cobalt chrome or any other suitable biocompatible metal. More specifically, a resorbable material such as magnesium may also be employed for the shaft 104 and the tip 112.

Figure 2:
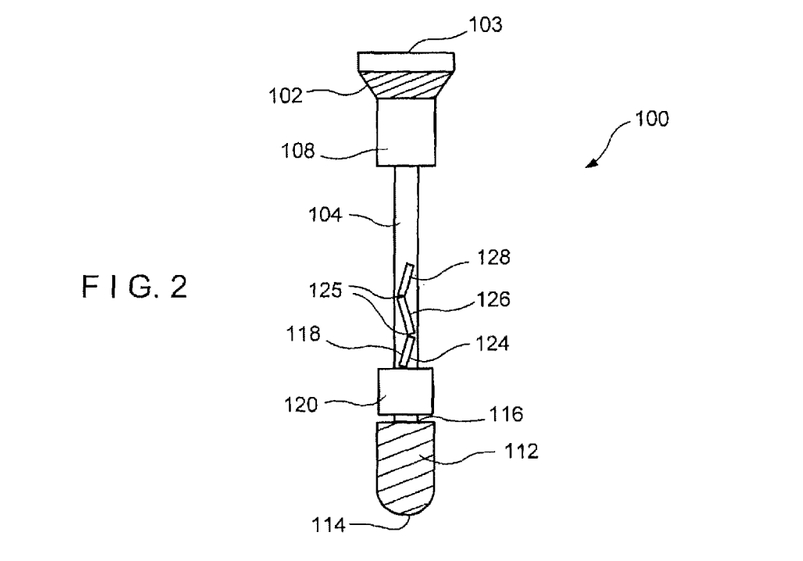
FIG. 2 shows a second partial cross-sectional view of the bone fixation device of FIG. 1.

A pair of wings 118 extend radially outward from the shaft 104 and are substantially slidable over a length thereof. The wings 118 include a substantially rectangular connector 120 with a width (i.e., an extent in a direction perpendicular to the longitudinal axis of the shaft) greater than a diameter of the extension 108 and the tip 112. A bore 122 extending through a center of the connector 120 is sized to permit insertion of the shaft 104 therethrough and defines two substantially evenly sized sections of the connector 120 on opposing lateral sides of the shaft 104, as shown in FIGS. 1 and 2. An inner wall of the bore 122 includes threading configured to engage threads formed on an outer wall of the shaft 104. When the shaft 104 is inserted in the bore 122, the connector 120 is screwably slidable proximally and distally along the shaft 104 but is prevented from moving laterally relative thereto. Each of the wings 118 further comprises arms 124, 126, 128 extending proximally from the proximal side of the connector 120 on opposite sides of the shaft 104. Specifically, the arms 124 are rotatably coupled to a proximal face of the connector 120 while the arms 126 are rotatably coupled to proximal sides of the arms 124 and the arms 128 are rotatably coupled to proximal sides of the arms 126. In this embodiment, the arms 124, 126 and 128 have substantially the same dimensions. It is further noted that although the exemplary embodiment of the present invention depicts three sets of arms 124, 126, 128, any number of arms may be included in the wings 118 without deviating from the spirit and scope of the present invention. The arms 124, 126 and 128 are defined by a series of bends or indentations 125 formed on each of the wings 118, the bends 125 defining areas of bendability when the wings 118 are subjected to a compressive force. In an unstressed position, the arms 124, 126, 128 extend in a single plane substantially parallel to the longitudinal axis of the shaft 104, as shown in FIG. 1. The arms 124 are connected to the connector 120 via pivotable connections permitting movement in a range of ±90° relative to longitudinal axis of the shaft 104 from the unstressed substantially parallel configuration. In a preferred embodiment, the wings 118 have a combined wingspan of approximately 13 mm. Furthermore, each of the arms 128, 126, 124 is movable in a range of ±90° relative to the adjacent arms 126, 124 and the connector 120, respectively. In a preferred embodiment, the wings 118. Furthermore, each of the arms 124, 126, 128 is separated from the shaft 104 by a space 130 configured to prevent contact between the arms 124, 126, 128 and the threads of the shaft 104. The wing 118 may be formed of a resorbable material including, but not limited to, magnesium, polylactide or polycaprolactone.

Figure 3:
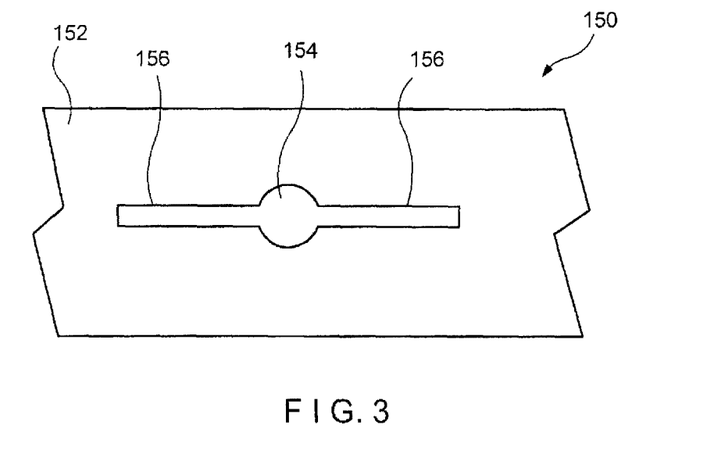
FIG. 3 shows a first top view of an exemplary bone plate hole for the bone fixation device of FIG. 1.
Figure 5:
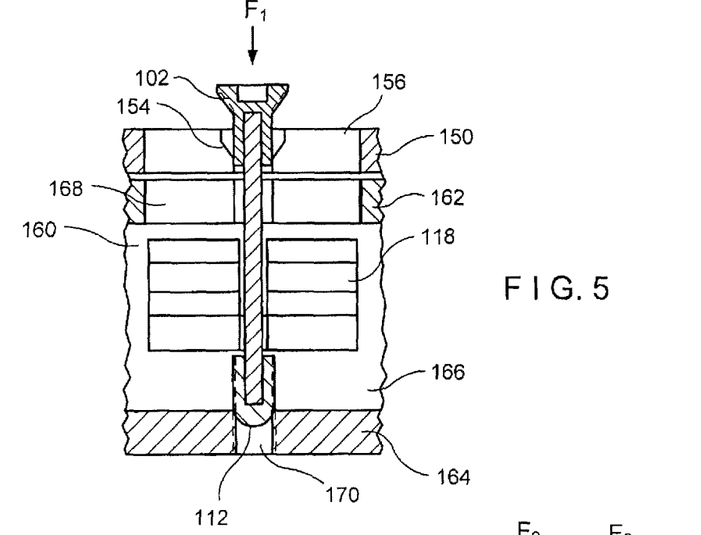
FIG. 5 shows a partial cross-sectional view of the bone fixation device of FIG. 1 in a first operative configuration.

FIG. 3 depicts a top view of an exemplary bone plate 150 for use with the bone fixation device 100 according to the present invention. The bone plate 150 comprises a substantially cylindrical hole 154 extending substantially therethrough at a desired angle from a non-bone facing surface 152 to a bone facing surface (not shown). As shown in the lateral cross-sectional view of FIGS. 5-8, the cylindrical hole 154 is formed with a taper matching a taper of the head 102 to permit insertion of the head 102 therein so that a proximal surface 103 of the head 102 lies flush with the non-bone facing surface 152. Furthermore, the cylindrical hole 154 and head 102 may comprise threading having an identical pitch to permit a screwable engagement therebetween. In another embodiment, each of the cylindrical hole 154 and the head 102 may be formed with two or more threads also formed with the same pitch. Similarly, the shaft 104 may be formed with threading having a pitch complementary to a threading of the bore 122 of the connector 120. A pair of elongated holes 156 extending laterally from opposite sides of the cylindrical hole 154 have dimensions selected to correspond to the dimensions of the wings 118 when the arms 124, 126 and 128 are arranged in a plane as shown in FIG. 5. Thus the hole 154 and the extending holes 156 permit insertion of the bone fixation device 100 through the bone plate 150. In an alternate embodiment of the present invention, the arms 124, 126, 128 and connector 120 may be offset with respect to the shaft 104 so that the wing 118 on one side of the shaft 104 is longer than a wing 118 on the other side of the shaft 104. In this embodiment, the elongated holes 156 may be formed with dimensions conforming to that of the wings 118 to permit insertion of the bone fixation device 100 into the cylindrical and elongated holes 154, 156, as those skilled in the art will understand. As will be described in greater detail with respect to the method described hereinafter, once inserted through the cylindrical and elongated holes 154, 156, the bone fixation device 100 is rotated so that the wings 118 are out of alignment with the elongated holes 156 to prevent disengagement of the bone fixation device 100 from the bone plate 150.

FIGS. 5-8 depict an exemplary method according to the present invention, wherein the bone fixation device 100 is inserted through the bone plate 150 which is situated over a target portion of a cortical bone 160 with a near cortex 162 and a far cortex 164, as those skilled in the art will understand. A middle region 166 of the bone 160 includes a medullary cavity, spongy bone layer, fat, etc. In a first step, the bone plate 150 comprising the cylindrical and elongated holes 154, 156 is positioned over a target portion of the bone 160 and the holes 154, 156 are aligned with a keyhole shaped bore 168 drilled into the bone 160. In an exemplary embodiment of the present invention, the bore 168 may be cut via a short pulsed diode pumped laser in the range of a 3 μm wavelength. The bore 168 extends through only the near cortex of the bone 160 and, as shown in FIG. 5, comprises a shape substantially matching a shape of the shaft 104 and the wings 118 to permit insertion of the bone fixation device 100 thereinto. A substantially cylindrical bore 170 is also cut into the far cortex at a position substantially aligned with the cylindrical portion of the bore 168 so that when the bone fixation device 100 is inserted into the bore 168 and screwed through the bone 160, the distal tip 112 thereof is received within the bore 170, as shown in FIG. 5.

Figure 4:
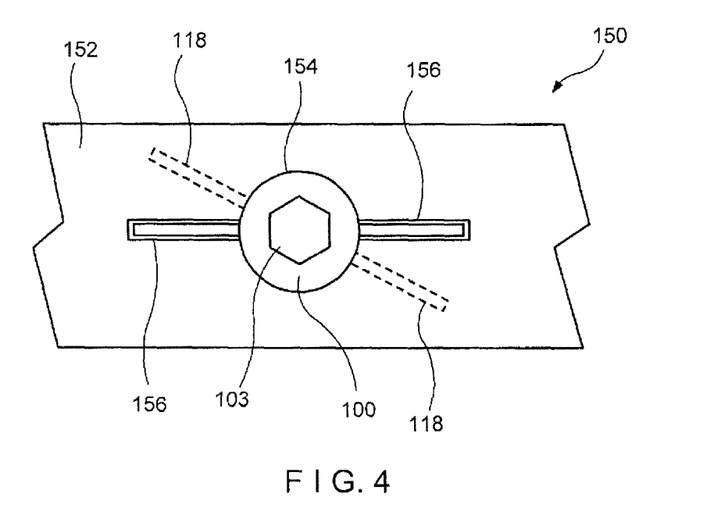
FIG. 4 shows a top view of the bone plate of FIG. 3 in an operative configuration.

As indicated above, the bone fixation device 100 is inserted through the cylindrical and elongated holes 154, 156 of the bone plate into the bore 168 and a driver (e.g., a screwdriver) (not shown) comprising a distal tip configured to engage the recess 103 of the bone fixation device 100 applies a force $F_1$ oriented to permit insertion of the bone fixation device 100 into the bone 160 in a position substantially aligned with the bores 168, 170. Specifically, due to the low material density of the middle region 166 of the bone 160, the bone fixation device 160 may simply be pushed therethrough. It is further noted that the wings 118 are initially positioned at a distalmost portion of the shaft 104. The wing 118 is able to maintain this position during insertion due to engagement of the threads of the bore 122 with threads of the shaft 104, as described in greater detail earlier. Once the bone fixation device 100 has been inserted to a position with the distal end 114 of the tip 112 lying adjacent to the bore 170, the bone fixation device 100 is rotated through a predetermined angle to move the wings 118 out of alignment with the bore 168, as shown in FIG. 4. The rotation may be facilitated by a driver 172 comprising a tapered tip 174 dimensioned to conform to the taper 106 of the head 102 or by a driver inserted into the recess 103 of the head 102, as those skilled in the art will understand. In a preferred embodiment, the bone fixation device 100 is rotated in a direction opposite the direction of threading formed on the shaft 104 so this rotation does not unscrew the shaft 104 relative to the connector 120. It is further noted that although FIG. 4 depicts rotation of the wing by an acute angle, the wings 118 may be rotated through any angle in the range of approximately 0-180° without deviating from the spirit and scope of the present invention so long as the wings 118 are not re-aligned with the bore 168.

Figure 6:
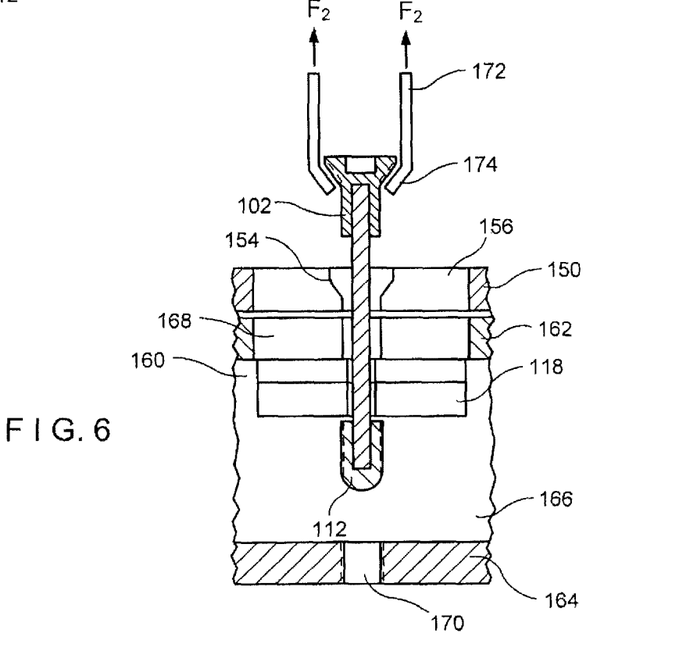
FIG. 6 shows a partial cross-sectional view of the bone fixation device of FIG. 1 in a second operative configuration.

The driver 172 then applies a force $F_2$ to the bone fixation device 100 being oriented in a direction substantially opposite the force $F_1$ partially withdraw the bone fixation device 100 from the bone 160. As the bone fixation device 100 moves proximally through the bone 160, the arms 124, 126, 128 of the wings 118 engage an inner wall of the substantially rigid near cortex 162 compressing the arms 124, 126, 128, and causing the arms 124, 126, 128 to fold flat relative to one another, as shown in FIG. 6. The folding of the arms 124, 126, 128 increases a contacting surface area of the wings 118 against the inner near cortex 162. Specifically, a length of each of the arms 124, 126, 128 along the longitudinal axis of the shaft 104 as shown in FIG. 5 is greater than a width thereof (i.e., a thickness thereof in a direction into the page in FIG. 5). In the unstressed configuration of FIG. 5, only the width face of the arm 128 is in contact with the inner near cortex 162. Folding of the arms 124, 126, 128 brings the length of the arm 128 into contact with the inner near cortex 162, increasing the resistance of the bone fixation device 100 to pull-out. The increase in contacting surface area also more evenly distributes forces applied to the bone fixation device 100 across the entire length of the wings 118, further deceasing the likelihood of pull-out.

Figure 7:
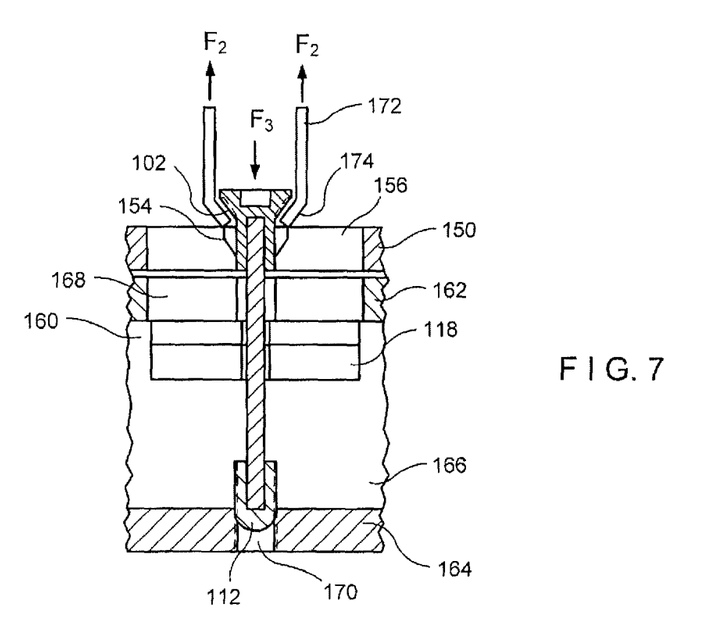
FIG. 7 shows a partial cross-sectional view of the bone fixation device of FIG. 1 in a third operative configuration.
Figure 8:
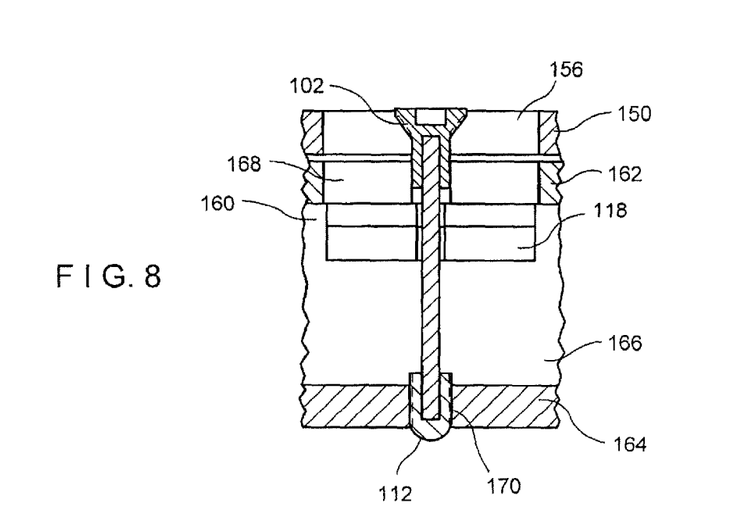
FIG. 8 shows a partial cross-sectional view of the bone fixation device of FIG. 1 in a fourth operative configuration.

As shown in FIG. 7, in a subsequent step, the force $F_2$ on the bone fixation device 100 is maintained while a clockwise rotational force $F_3$ is applied to the recess 103 to screw the bone fixation device 100 further distally into the bone 160. Maintenance of the force $F_2$ allows the wing 118 to maintain the compressed configuration while permitting the shaft 104 to be rotated relative to the connector 120 and into the bone 160 to a position wherein the distal tip 114 is substantially adjacent to the bore 170. Once the bone fixation device 100 has reached this position, the force $F_2$ may be removed since the pulling stress between the near cortex 162 and the far cortex 164 is now conserved. and only the force $F_3$ is applied to screw the tip 112 into the bore 170. The tip 112 is driven into the bore 170 until the head 102 of the bone fixation device 100 sits flush against the bone plate 150, as shown in FIG. 8 or until the threads of the head 102 engage the respectively formed threads of the hole 154.

Figure 9:
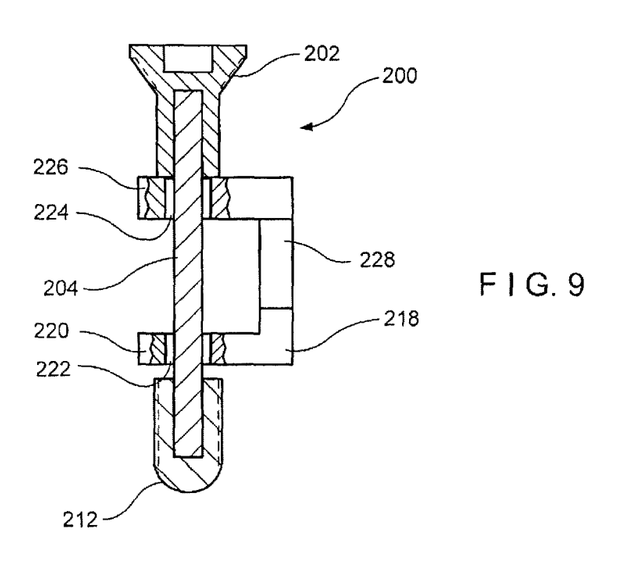
FIG. 9 shows a partial cross-sectional view of a bone fixation device according to a second embodiment of the present invention.
Figure 10:
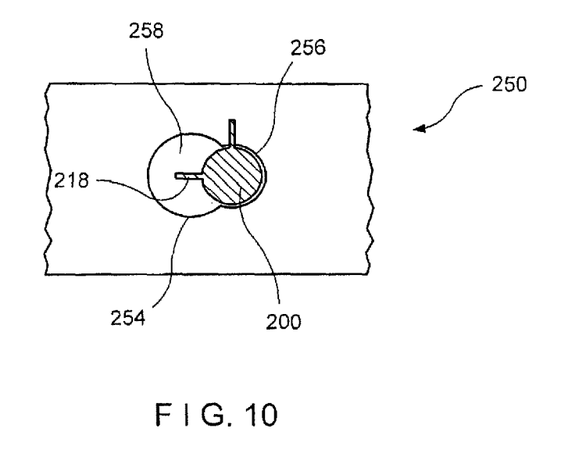
FIG. 10 shows a top view of an exemplary bone plate hole for the bone fixation device of FIG. 9.
Figure 11:
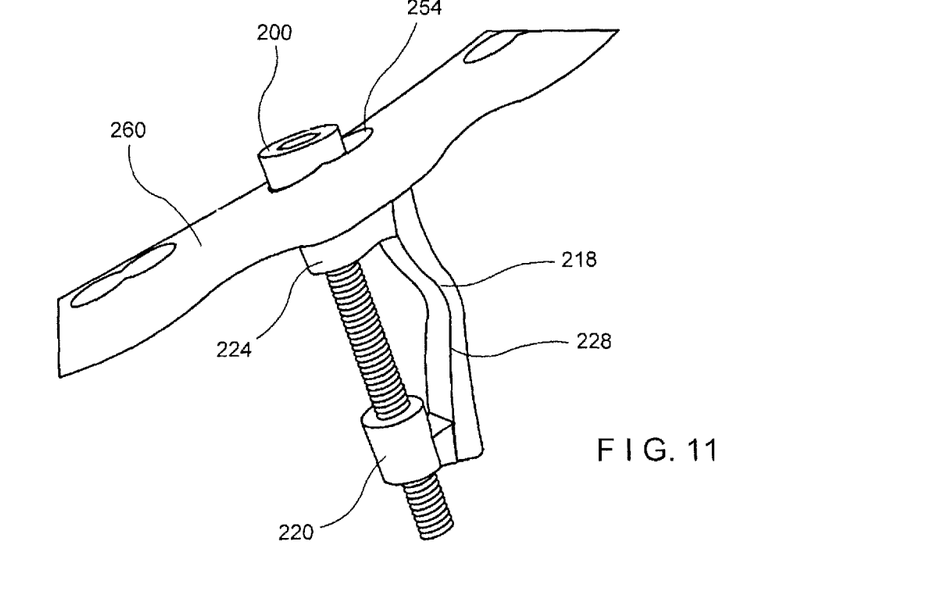
FIG. 11 shows a perspective view of the bone fixation device of FIG. 9 in a locked configuration.

FIGS. 9-11 depict a bone fixation device 200 according to a first alternate embodiment of the present invention, wherein the bone fixation device 200 is formed substantially similarly to the device 100 of FIG. 1 with the exception of the inclusion of only a single wing 218 extending from one side of the shaft 204. Specifically, the bone fixation device 200 comprises a head 202 attached to a shaft 204 with a tip 212 at a distal end thereof. A wing 218 extends from a first connector 220 at a distal end to a second connector 224 at a proximal end. Each of the first and second connectors 220, 224 project radially outward in the same direction from the shaft 204 with an arm 228 extending therebetween substantially parallel to a longitudinal axis of the shaft 204. The anti 228 is formed of a resorbable material including, but not limited to, magnesium, polylactide or polycaprolactone and is formed with a thickness of approximately 0.4-0.8 mm in the case of magnesium and approximately 0.6-1.5 mm in the case of a polymeric material to permit flexing thereof. Each of the first and second connectors 220, 224 is movable along the length of the shaft 204 independent of the other. Specifically, the first connector 220 comprises a bore 222 extending therethrough with threading in the bore 222 configured to engage threads of the shaft 204. The second connector 224 comprises a non-threaded bore 226 extending therethrough so that the second connector 224 is slidable over the shaft 204.

In a preferred embodiment, the bore 226 is formed with a substantial friction fit so that the second connector 226 slides along the shaft 204 upon application of at least a predetermined minimum compression force thereto, as will be described in greater detail hereinafter. As shown in FIG. 9, in an unstressed configuration, the first and second connectors 220, 224 are at opposing ends of the shaft 204 with the arm 228 straight so that a distance between the first and second connectors 220, 224 is substantially equivalent to a length of the shaft 204 minus the lengths of the first and second connectors 220, 224 along the shaft 204. It is noted however, that the distance between the first and second connectors 220, 224 and therefore also the length of the arm 228 may be modified without deviating from the spirit and scope of the present invention. The single-sided wing 218 is particularly advantageous in that it allows the bone fixation device 200 to be employed with any bone plate including a standard combination hole 254—i.e., no especially configured hole is required. Specifically, the head 202 and shaft 204 of the bone fixation device 200 may be dimensioned to permit the head 202 to be inserted in one of two substantially circular openings 256, 258 defined by the combination hole 254 with the wing 218 dimensioned to be inserted through the other of the openings 256, 258, as shown in FIG. 10.

An exemplary method of application of the bone fixation device 200 is substantially similar to the method described above with respect to FIGS. 1-8 wherein, after insertion into the combination hole 254, the wing 218 is rotated so that the arm 228 is out of alignment with the hole through which it was inserted and in contact with an inner near cortex of a target bone, as described in greater detail earlier and as shown in phantom in FIG. 10. Specifically, the bone fixation device 200 is first inserted into a bone (not shown) in which the near cortex has been drilled with a bore sized to permit insertion of the shaft 204 and wing 218 and in which the far cortex has been drilled with a substantially circular bore longitudinally aligned with an intended position of the head 202, as described in greater detail earlier. The bone fixation device 200 is then inserted through the opening 256 and into the bone until the tip 212 engages the inner wall of the far cortex. The bone fixation device 200 is then rotated by an angle sufficient to move the wing out of alignment with the opening 258, as shown in phantom in FIG. 10. A proximally directed force is applied to the head 202 drawing a portion of the bone fixation device 200 proximally out of the bone (not shown) and causing the arm 228 to bow as shown in FIG. 11 as the second connector 224 slides distally along the shaft 204 and moves closer to the first connector 220. The movement of the second connector 224 along the shaft 204 causes the wing 218 to recoil so that approximately half of the length of the wing lies substantially parallel to a plane of the inner near cortex, thus increasing a surface contacting area of the wing 218 therewith and increasing a holding strength of the bone fixation device 200 against the bone (not shown) and bone plate 250. In the next step, the proximally directed force is maintained on the bone fixation device 200 while a driver (not shown) is used to screw the bone fixation device 200 into the bone relative to the first connector 220. The bone fixation device assumes a locked position within the bone (not shown) when the tip 212 enters the bore formed in the far cortex (not shown).

Figure 12:
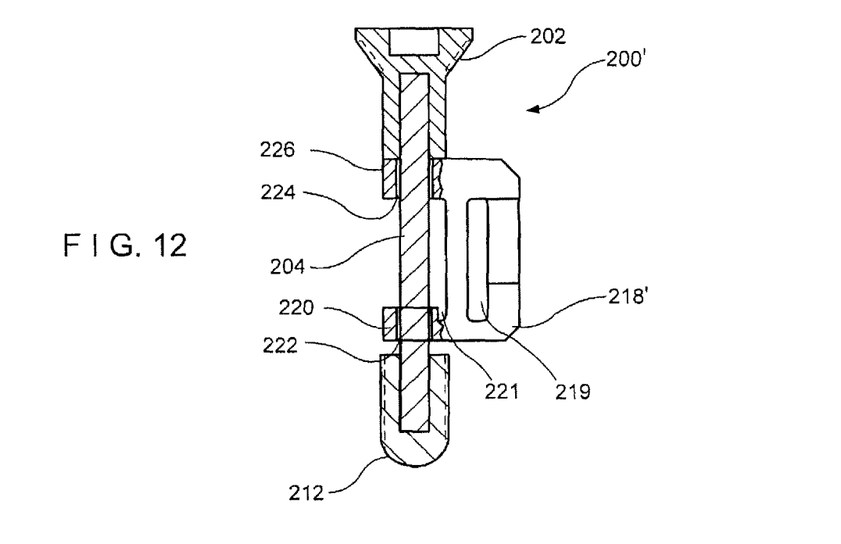
FIG. 12 shows a side view of a bone fixation device according to a third embodiment of the present invention.

FIG. 12 depicts another embodiment of the present invention wherein a bone fixation device 200' is formed substantially similarly to the bone fixation device 200 of FIGS. 9-11, with similar elements identified by the same reference numerals. The bone fixation device 200' comprises a wing 218' formed substantially similarly to the wing 218 with the exception of a first opening 219 formed therethrough. The first opening 219 has a substantially rectangular shape corresponding to a substantially rectangular shape of the wing 218'. The first opening 219 reduces a structural strength of the wing 218' so that a lower amount of mechanical force (e.g., the pulling force $F_2$) is required to cause a folding thereof, as described in greater detail earlier. The wing 218' further comprises a second opening 221 formed adjacent the shaft 204 preventing contact between the shaft 204 and the wing 218'. In an exemplary embodiment, the wing 218' and the connector 220 have a combined width of approximately 9 mm and a longitudinal length of approximately 33 mm. Furthermore, the connector 220 has a longitudinal length of approximately 5 mm while the bore 226 has a longitudinal length of approximately 3 mm. Each of the connector 220 and the bore 226 may have a diameter of approximately 5 mm. The wing 218' may be approximately 1 mm in thickness. It is noted however, that the aforementioned measurements are exemplary only and are not meant to limit the scope of the invention. The measurements may be varied to accommodate a particular bone being treated. For example, whereas the present invention has been described with respect to larger bones (e.g., humerus, femur, tibia, spinal vertebrae, pelvis), the measurements may be reduced by any proportions and percentages (e.g., reduced by 80%) to accommodate procedures for smaller bones (e.g., radius, ulna, skull). The bone fixation device 200' is employed in the same manner discussed above with respect to FIGS. 9-11.

Figure 13:
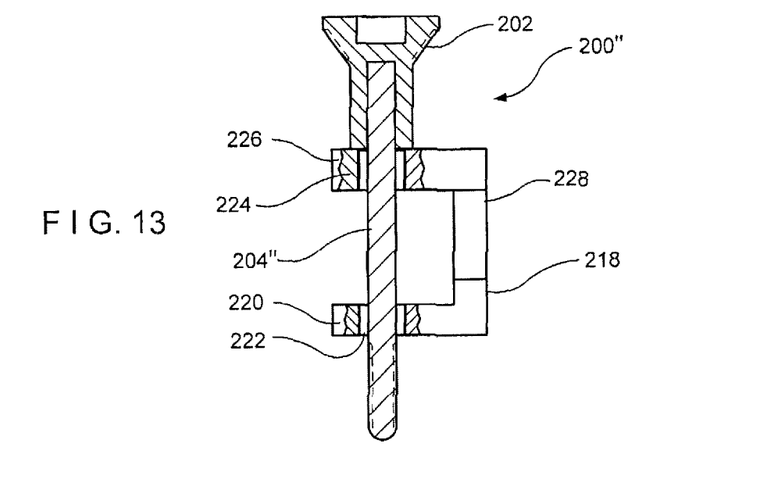
FIG. 13 shows a partial cross-sectional view of a bone fixation device according to a fourth embodiment of the present invention.

FIG. 13 depicts another embodiment of the present invention wherein a bone fixation device 200" is formed substantially similarly to the bone fixation device 200 of FIGS. 9-11, with similar elements identified by the same reference numerals. The bone fixation device 200" does not include an increased diameter tip 212 at a distal end thereof but rather, comprises a shaft 204" with a substantially uniform diameter throughout its length. The bone fixation device 200" is employed in the same manner discussed above with respect to FIGS. 9-11.

Figure 14:
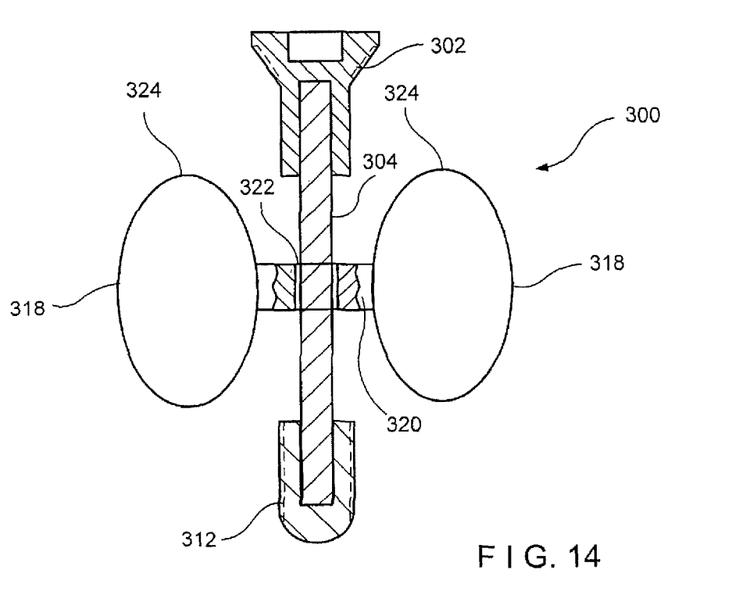
FIG. 14 shows a partial cross-sectional view of a bone fixation device according to a fifth embodiment of the present invention.

FIG. 14 depicts a bone fixation device 300 according to yet another embodiment of the present invention. The bone fixation device 300 is formed substantially similarly to the bone fixation device 100 except that the wings 318 of the bone fixation device 300 are oval in shape. Specifically, the bone fixation device 300 comprises a head 302, shaft 304 and tip 312 formed substantially similarly to the components of the bone fixation device 100 shown in FIGS. 1-8. A connector 320 comprising a threaded bore 322 engages threads of the shaft 304 and includes arms 324 separated radially therefrom. Each of the arms 324 has a cross-section in a plane parallel to the longitudinal axis of the shaft 304 that is substantially oval. An exemplary method of application of the bone fixation device 300 is substantially similar to the method discussed above with respect to FIGS. 1-8, including application of a compressive force to press a portion of each wing 318 extending proximally of the connector 320 against an inner wall of the near cortex of a bone into which it is inserted compressing the arms 324 to increase a contacting surface area thereof. An exemplary plate hole for use with the bone fixation device 300 is also formed substantially similarly to the bone plate 150 except that the elongated hole portions 156 are sized to permit insertion of the wings 318 therethrough. It is further noted that the wings according to this invention may assume any shape providing favorable folding/compressing properties when pressed against the near cortex including, but not limited to, circular or square, etc.

Figure 15:
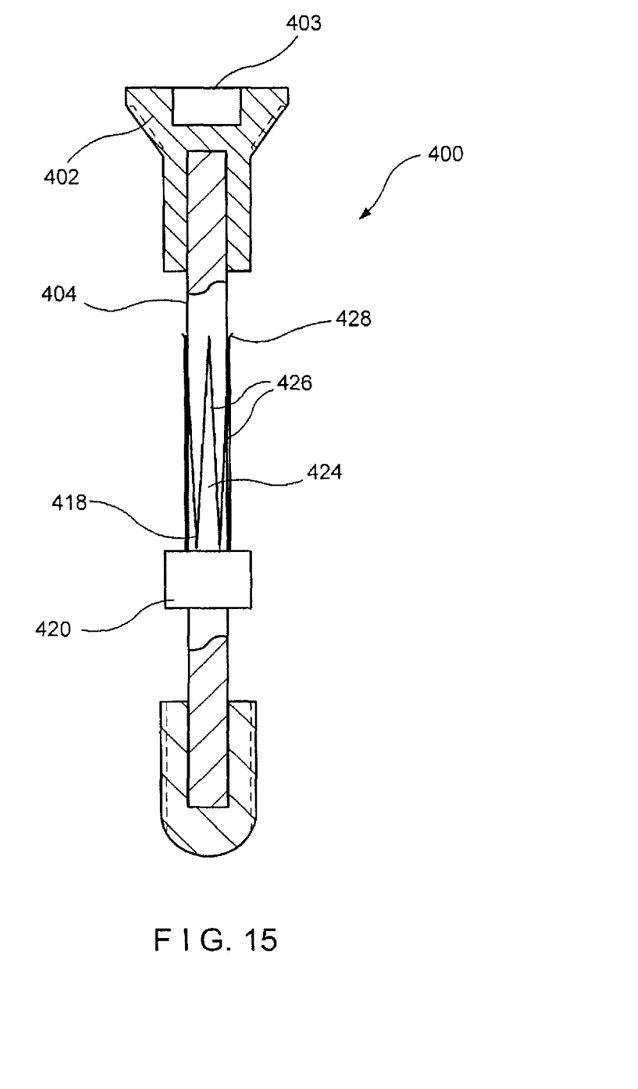
FIG. 15 shows a partial cross-sectional view of a bone fixation device according to a sixth embodiment of the present invention.

In yet another alternate embodiment of the present invention, the wings may comprise any shape configured to expand over the inner surface of the near cortex upon application of an axially directed pressure thereto. In one such embodiment, as shown in FIG. 15, a bone fixation device 400 comprises an umbrella-shaped wing 418. The bone fixation device is substantially similar to the bone fixation device 100 of FIG. 1 except as noted and comprises a head 402 with an elongated shaft 404 extending distally therefrom. The wing 418 is formed as a series of ribs 424 extending proximally from a connector 420 substantially similar to the connector 120 of FIG. 1. Adjacent pairs of the ribs are connected to one another at proximal ends thereof so that a plurality of substantially triangular arms 426 are defined. It is noted however, that the arms 426 may also be rectangular in shape and formed of a metal or polymeric material attached to the connector 420 at distal ends thereof. The distal ends of the ribs 424 are attached to the connector 420 by a spring-like mechanism (not shown) biasing the ribs to lie substantially parallel to the shaft 404 in a first configuration. Alternately, the arms 426 may be pre-bent to bias proximal ends thereof radially outward so that, when being inserted distally into the bone, the arms are held against the shaft 404 and, when retracted proximally, the arms 426 extend further radially outward. In the first configuration, the wing 418 is configured to be slidably inserted into a substantially circular plate hole (not shown). Proximal ends of each of the triangular arms 426 comprise flared tips 428 extending radially away from the shaft 404. The flared tips 428 are formed of a substantially flexible material that is retracted against the shaft 404 when the bone fixation device 400 is being inserted through the plate hole (not shown). Furthermore, the flared tips 428 may be biased to project radially away from the shaft 404 beyond a periphery of the plate hole (not shown). Thus, when the bone fixation device (400) is moved out of the plate hole (not shown), engagement of the flared tips 428 with an inner cortex of the bone causes the ribs to pivot radially outward until the ribs 424 lie in a plane substantially perpendicular to a longitudinal axis of the shaft 404 in direct contact with the inner cortex. In a further step, the withdrawal force on the bone fixation device 400 is maintained while a clockwise rotational force is applied to a recess 403 to screw the bone fixation device 400 relative to the connector 420, which comprises threading formed on an inner wall thereof and into the bone (not shown). Maintenance of the withdrawal force allows the wing 418 to maintain the radially expanded configuration while permitting the shaft 404 to be rotated relative to the connector 420 to screw the bone fixation device 400 to a desired position while the engagement of the flared tips 428 with the inner cortex.

Figure 16:
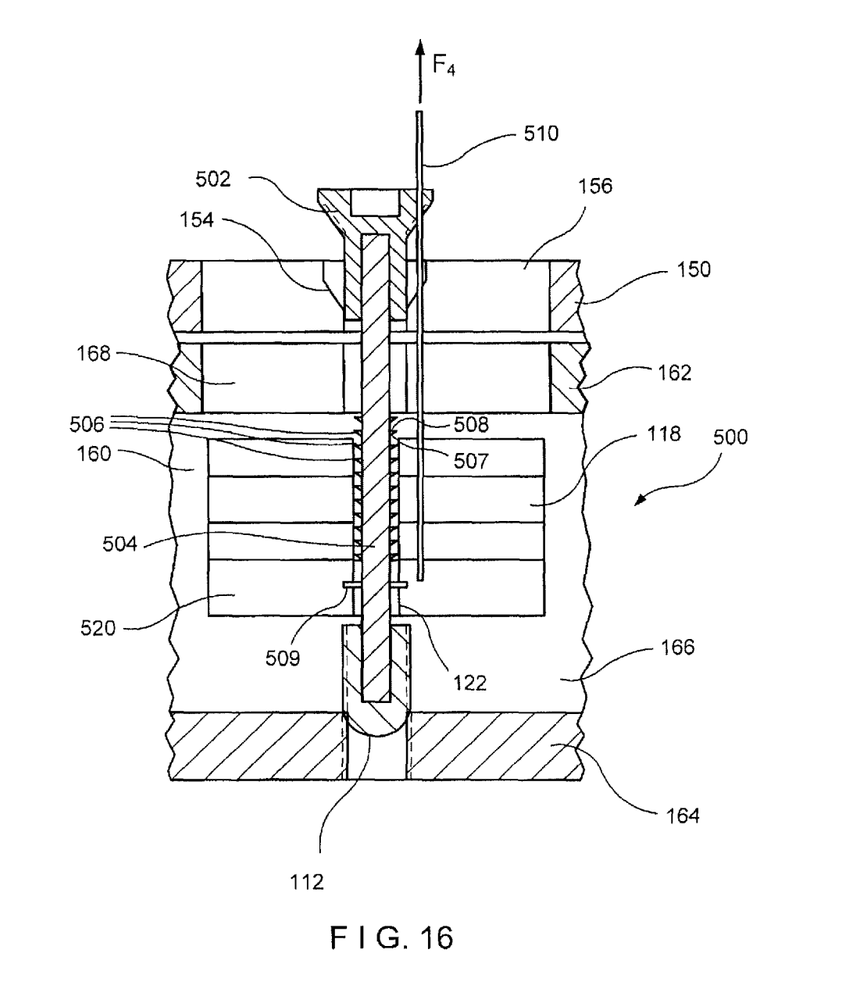
FIG. 16 shows a partial cross-sectional view of a bone fixation device according to a seventh embodiment of the present invention.

FIG. 16 depicts a bone fixation device 500 according to yet another embodiment of the present invention. Except as pointed out below, the bone fixation device 500 is formed substantially similarly to the bone fixation device 100 of FIG. 1 with like elements referred to by the same reference numerals. The bone fixation device 500 comprises a shaft 504 including a plurality of teeth 506 in place of the threading of the shaft 104. The teeth 506 may be formed as ringed projections extending radially outward from the shaft 504 separated from one another by a predetermined distance along an axis thereof. The teeth 506 may be distributed over substantially the entire length of the shaft 104 with each tooth comprising first and second angled faces 507, 508, respectively, with the first face 507 angled proximally from the shaft 504 so that a connector 520 may be slid proximally thereover in a ratchet-type movement, as those skilled in the art will understand. The second face 508 of each tooth extends radially from the shaft 504 substantially perpendicular to a longitudinal axis of the shaft 504 to lock the connector 520 against distal movement thereover. The connector 520 includes a radial abutment 509 extending into a bore 522 thereof by a distance sufficient to permit engagement with the teeth 506 of the shaft 504 so that, as the connector 520 is moved proximally over the teeth 506, the abutment 509 is deflected radially outward by the first faces 507 and lockingly engaged by the second faces 508. The connector 520 may further comprise a tensioning member 510 (e.g., a suture) extending proximally therefrom and following a path substantially adjacent to the shaft 504 with a proximal end of the cable 510 extending proximally of a head 502 accessible to a physician or other user of the device. When the tensioning member 510 is pulled proximally, the connector 520 is slid proximally over the teeth 506 until the connector 520 is locked in a desired position within the bone 160.

In accordance with an exemplary embodiment of the present embodiment, the bone fixation device 500 is first inserted to a target depth in the bone 160 until the tip 112 is received within the bore 170 of the far cortex, as described in greater detail earlier. During insertion, the connector 520 and wings 118 are located at a distalmost position along the shaft 504, as shown in FIG. 16. After insertion, the shaft 504 is rotated by a predetermined angle to move the wings 118 out of alignment with the bore 168. A proximally directed force $F_4$ is then applied to the tensioning member 510 to draw the connector 520 and the wings 118 proximally until the wings 118 are longitudinally compressed against the near cortex 162 with the abutment 509 engaging the second face 508 of one of the teeth 506 to prevent the connector 520 from sliding distally over the shaft 504 locking a position of the bone fixation device 500 within the bone 160.

Although the present invention has been described with reference to preferred embodiments, it is submitted that various modifications can be made to the exemplary system and method without departing from the spirit and scope of the invention.

What is claimed is:

1. A bone fixation device, comprising:
a threaded shaft extending along a longitudinal axis from a proximal end to a distal end;
a head located at the proximal end of the shaft;
a connector threadably engaging the threaded shaft and movable therealong; and
an extension member rotatably movable along an axis parallel to the longitudinal axis of the threaded shaft, the extension member including a portion rotatable about the threaded shaft between an insertion configuration for insertion through an opening in a cortex of a bone to a locked configuration when pressed against an inner surface of the cortex, a profile of the portion of the extension member in the locked configuration in a plane perpendicular to the longitudinal axis of the shaft being increased relative to a profile of the portion of the extension member in the insertion configuration to distribute forces transmitted between the bone fixation apparatus and the bone over an increased area of the cortex, wherein a radial extent of the portion of the extension member remains the same in the insertion and locked configurations.

2. The device of claim 1, wherein said portion of the extension member comprises a first wing extending radially outward from the connector on a first side of the shaft wherein an extent of the first wing in a direction perpendicular to a radial extent of the first wing from the connector is greater in the locked configuration than in the insertion configuration.

3. The device of claim 2, wherein said portion of the extension member further comprises a second wing extending radially outward from the connector on a side of the shaft opposite the first wing wherein an extent of the second wing in a direction perpendicular to a radial extent of the second wing from the connector is greater in the locked configuration than in the insertion configuration.

4. The device of claim 2, wherein the first wing extends further radially from the shaft than the head.

5. The device of claim 2, wherein the first wing extends proximally from the connector by a greater distance in the insertion configuration than in the locked configuration.

6. The device of claim 2, wherein the first wing is configured to move from the insertion configuration to the locked configuration through the application of a proximally directed force against the head.

7. The device of claim 2, wherein the first wing includes a plurality of arms rotatably coupled to one another, the arms being biased toward the insertion configuration.

8. The device of claim 7, wherein the arms are folded over one another in the locked configuration so that a surface of a proximal-most one of the arms which, in the insertion configuration, extends in a plane substantially parallel to the longitudinal axis extends in a plane perpendicular to the longitudinal axis.

9. The device of claim 2, wherein the first wing includes one of magnesium, polylactide and polycaprolactone.

\* \* \* \* \*

UNITED STATES PATENT AND TRADEMARK OFFICE
CERTIFICATE OF CORRECTION

PATENT NO. : 9,844,403 B2  
APPLICATION NO. : 12/857034  
DATED : December 19, 2017  
INVENTOR(S) : Nardini Page 1 of 1

It is certified that error appears in the above-identified patent and that said Letters Patent is hereby corrected as shown below:

In the Claims

Claim 8, Column 11, Lines 1-2:
"configuration, extends in a plane substantially parallel to the longitudinal axis extends in a plane perpendicular to the"

Should read:
"configuration extends in a plane substantially parallel to the longitudinal axis, extends in a plane perpendicular to the".

Signed and Sealed this
Twenty-eighth Day of May, 2019

Andrei Iancu
*Director of the United States Patent and Trademark Office*